United States Patent
Burbar et al.

(10) Patent No.: US 12,138,096 B2
(45) Date of Patent: Nov. 12, 2024

(54) PARTIAL SCAN AND RECONSTRUCTION FOR A POSITRON EMISSION TOMOGRAPHY SYSTEM

(71) Applicant: Siemens Medical Solutions USA, Inc., Malvern, PA (US)

(72) Inventors: Ziad Burbar, Knoxville, TN (US); Inki Hong, Knoxville, TN (US); Stefan B. Siegel, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 348 days.

(21) Appl. No.: 17/597,992

(22) PCT Filed: Jan. 10, 2020

(86) PCT No.: PCT/US2020/013000
§ 371 (c)(1),
(2) Date: Feb. 1, 2022

(87) PCT Pub. No.: WO2021/141590
PCT Pub. Date: Jul. 15, 2021

(65) Prior Publication Data
US 2022/0287670 A1  Sep. 15, 2022

(51) Int. Cl.
*A61B 6/00* (2024.01)
*A61B 6/03* (2006.01)
*A61B 6/46* (2024.01)

(52) U.S. Cl.
CPC ............ *A61B 6/5235* (2013.01); *A61B 6/032* (2013.01); *A61B 6/037* (2013.01); *A61B 6/469* (2013.01); *A61B 6/5205* (2013.01)

(58) Field of Classification Search
CPC ....... A61B 6/5235; A61B 6/032; A61B 6/037; A61B 6/469; A61B 6/5205; G06T 2211/464; G06T 11/005
See application file for complete search history.

(56) References Cited

U.S. PATENT DOCUMENTS

| | | | |
|---|---|---|---|
| 2014/0095106 A1* | 4/2014 | Wang | A61B 6/037 702/157 |
| 2016/0358334 A1* | 12/2016 | Osborne | G06T 5/73 |
| 2018/0000435 A1* | 1/2018 | Liu | A61B 6/5235 |
| 2018/0308264 A1* | 10/2018 | Gu | G06T 7/11 |

(Continued)

OTHER PUBLICATIONS

Markiewicz, Pawel J et al: "NiftyPET: a High-throughput Software Platform for High Quantitative Accuracy and Precision PET Imaging and Analysis", Neuroinformatics, Humana Press Inc, Boston, vol. 16, No. 1, Dec. 26, 2017, pp. 95-115.

(Continued)

*Primary Examiner* — Amara Abdi (57) ABSTRACT

A method for performing a partial scan of a patient using a PET/CT system includes receiving a selection of a region of interest for scanning and performing a CT scan over a region of interest with the PET/CT system to acquire raw CT data. The raw CT data is reconstructed into one or more CT images. The PET/CT system is configured to limit data collection to the region of interest. A PET scan limited to a region of interest is performed with the PET/CT system to acquire raw PET data. The raw PET data is reconstructed into one or more PET images of the region of interest.

18 Claims, 7 Drawing Sheets

(56) References Cited

U.S. PATENT DOCUMENTS

| | | | |
|---|---|---|---|
| 2019/0066342 A1* | 2/2019 | Zhu | G06T 11/005 |
| 2019/0070437 A1* | 3/2019 | Olcott | A61N 5/1081 |
| 2019/0361136 A1* | 11/2019 | Song | G01T 1/249 |
| 2020/0000425 A1* | 1/2020 | Ji | A61B 6/488 |
| 2021/0074036 A1* | 3/2021 | Fuchs | A61B 6/032 |
| 2021/0110583 A1* | 4/2021 | Lee | G06T 11/008 |

OTHER PUBLICATIONS

International Search Report received for Corresponding PCT Application No. PCT/US2020/013000, dated Aug. 13, 2020.

\* cited by examiner

PARTIAL SCAN AND RECONSTRUCTION FOR A POSITRON EMISSION TOMOGRAPHY SYSTEM

TECHNICAL FIELD

The present disclosure relates generally to methods, systems, and apparatuses for performing a partial scan and reconstruction in a positron emission tomography (PET) system or a combined Computed Tomography (CT)/PET system. The techniques described herein may be applied, for example, to enable long axial field of view imaging.

BACKGROUND

Nuclear medicine uses radiation emission to acquire images that show the function and physiology of organs, bones or tissues of the body. Radiopharmaceuticals are introduced into the body by injection or ingestion. These radiopharmaceuticals are attracted to specific organs, bones, or tissues of interest. The radiopharmaceuticals cause gamma photons to emanate from the body, which are then captured by a detector. The interaction of the gamma photons with a scintillation crystal of the detector produces a flash of light. The light is detected by an array of optical sensors of the detector.

Positron emission tomography (PET) is a nuclear medicine imaging technique that uses a positron emitting radionuclide. PET is based on coincidence detection of two gamma photons produced from positron-electron annihilation. The two gamma photons travel in generally opposite directions from the annihilation site, and can be detected by two opposing detectors of a ring of detectors. Annihilation events are typically identified by a time coincidence in the detection of the two gamma photons. The opposing detectors identify a line-of-response (LOR) along which the annihilation event occurred.

PET may be combined with another imaging modality in a multimodality system. Such multimodality imaging systems may have diagnostic value. PET-computed tomography (CT) multimodality imaging systems allow scans to be performed back-to-back or in a same coordinate system and with similar timing. The axial fields of view of the individual modalities are typically as close together as possible in order to minimize the impact of patient motion and increase spatial correlation of the respective data sets. PET-CT and multimodality systems commonly combine the benefits of a high local resolution modality (e.g., CT imaging) with a modality with high functional sensitivity (e.g., PET) to spatially align detailed anatomy and functional information.

Historically, PET/CT systems were designed with axial fields-of-view (aFoV) that matched organs of interest, such as the heart or brain. For larger imaging volumes, the patient would be scanned at various axial positions, either by step-and-shoot or continuous bed position. As there is a move towards longer aFoV systems, the expectation is that there must be a CT dataset that matches the aFoV of the PET tomograph for attenuation and scatter correction. However, such long, detailed CT scans could subject the patient to high doses of radiation.

Accordingly, it is desired to provide a way of minimizing the dose to the patient, while still collecting enough data to cover the area/organ of interest.

SUMMARY

Embodiments of the present invention address and overcome one or more of the above shortcomings and drawbacks, by providing methods, systems, and apparatuses related to performing a partial scan and reconstruction in a positron emission tomography (PET) system or a combined Computed Tomography (CT)/PET system. More specifically, the techniques described herein minimize the CT dose to the patient by scanning the minimum extent required to cover the area/organ of interest, and only reconstructing the volume defined by that area of interest.

According to some embodiments, a method for performing a partial scan of a patient using a PET/CT system includes receiving a selection of a region of interest for scanning and performing a CT scan over a region of interest with the PET/CT system to acquire raw CT data. The raw CT data is reconstructed into one or more CT images. The PET/CT system is configured to limit data collection to the region of interest. A PET scan limited to a region of interest is performed with the PET/CT system to acquire raw PET data. The raw PET data is reconstructed into one or more PET images of the region of interest.

According to other embodiments, a method for performing a partial scan of a patient using a PET/CT system includes receiving a selection of a region of interest for scanning, and performing a CT scan over a region of interest with the PET/CT system to acquire raw CT data. The raw CT data is reconstructed into one or more CT images. One or more radial offset values and a restricted ring difference describing the region of interest in a coordinate space of the PET/CT system are identified. A PET scan is performed with the PET/CT system to acquire raw PET data. A reconstruction of the raw PET data limited to the region of interest is performed to yield one or more PET images.

According to other embodiments, a method for performing a partial scan of a patient using a PET/CT system includes receiving a selection of a region of interest for scanning and performing a CT scan over a region of interest with the PET/CT system to acquire raw CT data. The raw CT data is reconstructed into one or more CT images. A PET scan is performed with the PET/CT system to acquire raw PET data. A reconstruction of the raw PET data limited to the region of interest is performed to yield one or more PET images.

According to other embodiments, a system for performing a partial scan of a patient includes one or more operator consoles, a CT subsystem, and a PET subsystem. The operator consoles are configured to receive a selection of a region of interest for scanning. The CT subsystem is configured to perform a CT scan over a region of interest to acquire raw CT data, and reconstruct the raw CT data into one or more CT images. The PET subsystem is configured to adjust one or more hardware elements of the PET subsystem to limit data collection to the region of interest, and perform a PET scan limited to a region of interest to acquire raw PET data. The raw PET data is reconstructed into one or more PET images of the region of interest.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

The following disclosure describes the present invention according to several embodiments directed at methods, systems, and apparatuses for performing a partial scan and reconstruction in a positron emission tomography (PET) system or a combined Computed Tomography (CT)/PET system. The techniques described herein may be applied, for example, to enable long axial field of view imaging. Briefly, a CT topogram is acquired to help the user define the region of interest. A CT scan is then performed for the selected area of interest, with sufficient overscanning for attenuation and scatter correction. Then, various techniques can be applied to perform a partial PET scan. In some embodiments, the partial scan is performed by only collecting data from PET detectors covering the area of interest and satisfying a desired ring difference. This may be accomplished, for example, by disabling the detectors which fall outside the associated area of interest or programming the coincidence electronics to only pass data from lines-of-response (LOR) which cross the area of interest. In other embodiments, the partial scan is performed by first acquiring the data normally, and then restricting histogramming to LORs which cross the area of interest. In still other embodiments, data acquisition and histogramming are both performed in a conventional manner, and reconstruction of the resultant sinogram is limited to the area of interest. With each of the techniques discussed above, there will be significantly lower patient does from the CT scan. Additionally, because less data needs to be collected and stored as images, the techniques discussed above save storage space, speed up any subsequent processing, and speed up data transfer generally.

Figure 1:
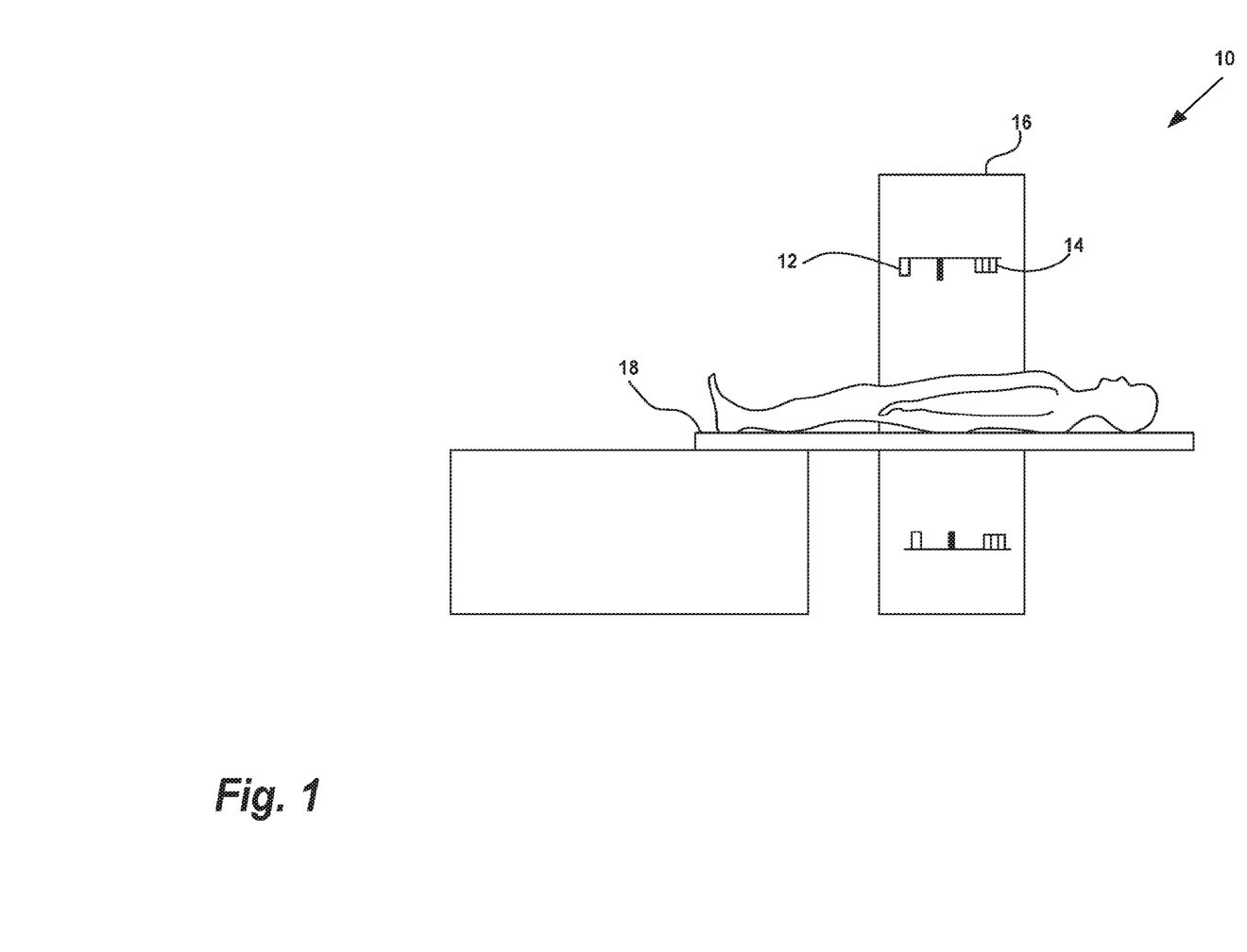
FIG. 1 is a schematic diagram of the side view of the PET/CT scanner of the present invention showing the CT scanner and PET scanner disposed within a single gantry.
Figure 2A:
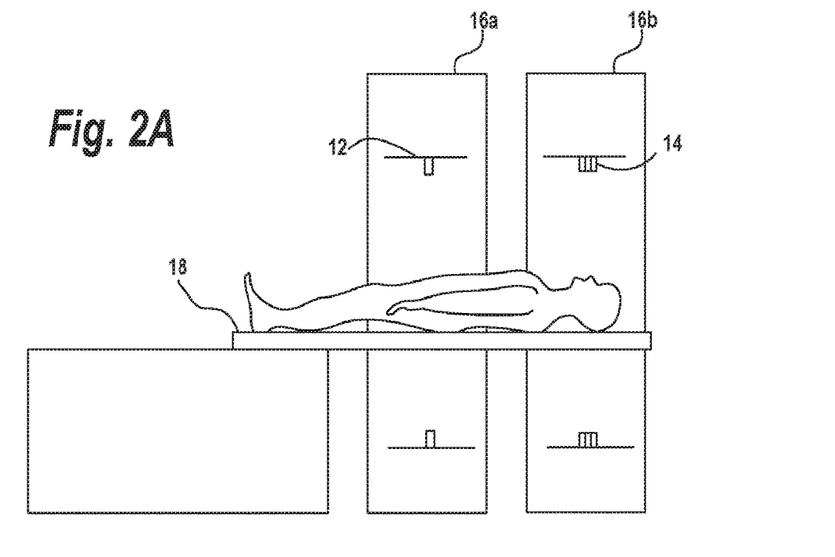
FIG. 2A illustrates an alternate embodiment wherein the X-ray CT and PET tomograph detectors are disposed in separate gantries which are fixed relative to each other and the patient bed is movable between the gantries.
Figure 2B:
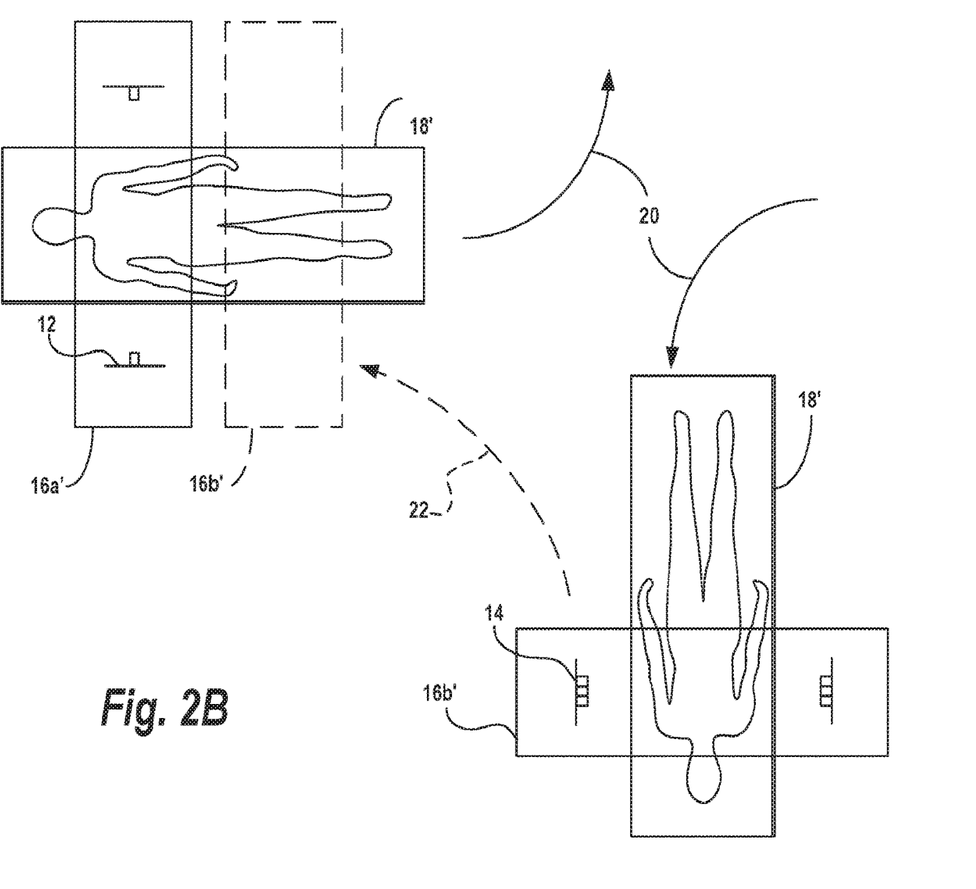
FIG. 2B illustrates a further alternate embodiment wherein the X-ray and PET tomograph detectors are disposed in separate gantries, either of which is movable with respect to the other, and wherein the patient bed is movable with respect to each gantry.

FIGS. 1, 2A, and 2B illustrate an example combined PET and X-Ray CT tomograph 10, that may be used in some embodiments of the present invention. The combined PET and X-Ray CT tomograph, or PET/CT scanner 10 allows registered CT and PET images to be acquired sequentially in a single device, overcoming alignment problems due to internal organ movement, variations in scanner bed profile, and positioning of the patient for the scan.

In this example, the PET/CT scanner 10 combines a CT scanner 12 with a PET scanner 14. The PET/CT scanner 10 includes a PET scanner 14 and a CT scanner 12, both commercially-available, in a physically known relationship one with the other. Each of the X-ray CT scanner 12 and the PET scanner 14 are configured for use with a single patient bed 18 such that a patient may be placed on the bed 18 and moved into position for either or both of an X-ray CT scan and a PET scan.

In the illustrated embodiment of FIG. 1, the completed PET/CT scanner comprises X-ray CT detectors 12 and PET tomograph detectors 14 being disposed within a single gantry 16, and wherein a patient bed 18 is movable therein to expose a selected region of the patent to either or both scans. In a commercial PET/CT scanner 10, the detectors 14 can vary in axial length. Historically, the detector 14 axial length can vary from 16 cm to 26 cm. Currently, there is a need for a PET scanner 16B where the axial FoV or the length of detectors 14 is longer than the standard scanners such as 50 cm-200 cm.

In a second instance, illustrated in FIG. 2A, the X-ray CT and PET tomograph detectors 12, 14 are disposed in separate gantries 16A, B which are fixed relative to each other, and wherein the patient bed 18 is movable between the gantries 16A, B. In a third instance, illustrated in FIG. 2B, the X-ray and PET tomograph detectors 12, 14 are disposed in separate gantries 16A', B', either of which is movable with respect to the other, wherein the patient bed 18' is movable with respect to each gantry 16A', B', as indicated by the arrows 20. Alternatively, one or both gantries 16A', B' may be moved relative to the patient bed 18' and the other of the gantries 16A', B' as indicated by the arrow 22. In each of these embodiments as illustrated in FIGS. 1, 2A, and 2B, the patient is placed on a single patient bed 18 for either or both scans, with either or all of the scanning devices and the patient bed is/are moved to accomplish the required scan(s).

In some embodiments, the combined PET and X-Ray CT tomograph may include an operator interface (not shown in FIGS. 1, 2A, and 2B) to provide data processing and user interface functions. The data processing and user interface functions may be provided separately in other embodiments. For example, image reconstruction and other processing of the scan data may be implemented by a separate computing system. The PET and CT subsystems may be supported by respective operator consoles and/or computing systems. The operator console may be in communication with the gantry controller and the data acquisition system to control the operation of the combined PET and X-Ray CT tomograph. The gantry controller may be integrated with the operator console to any desired extent. In some embodiments, the operator console is configured to process PET and CT scan data provided by the data acquisition system. In other embodiments, a separate computing system may be provided for such processing.

Figure 3:
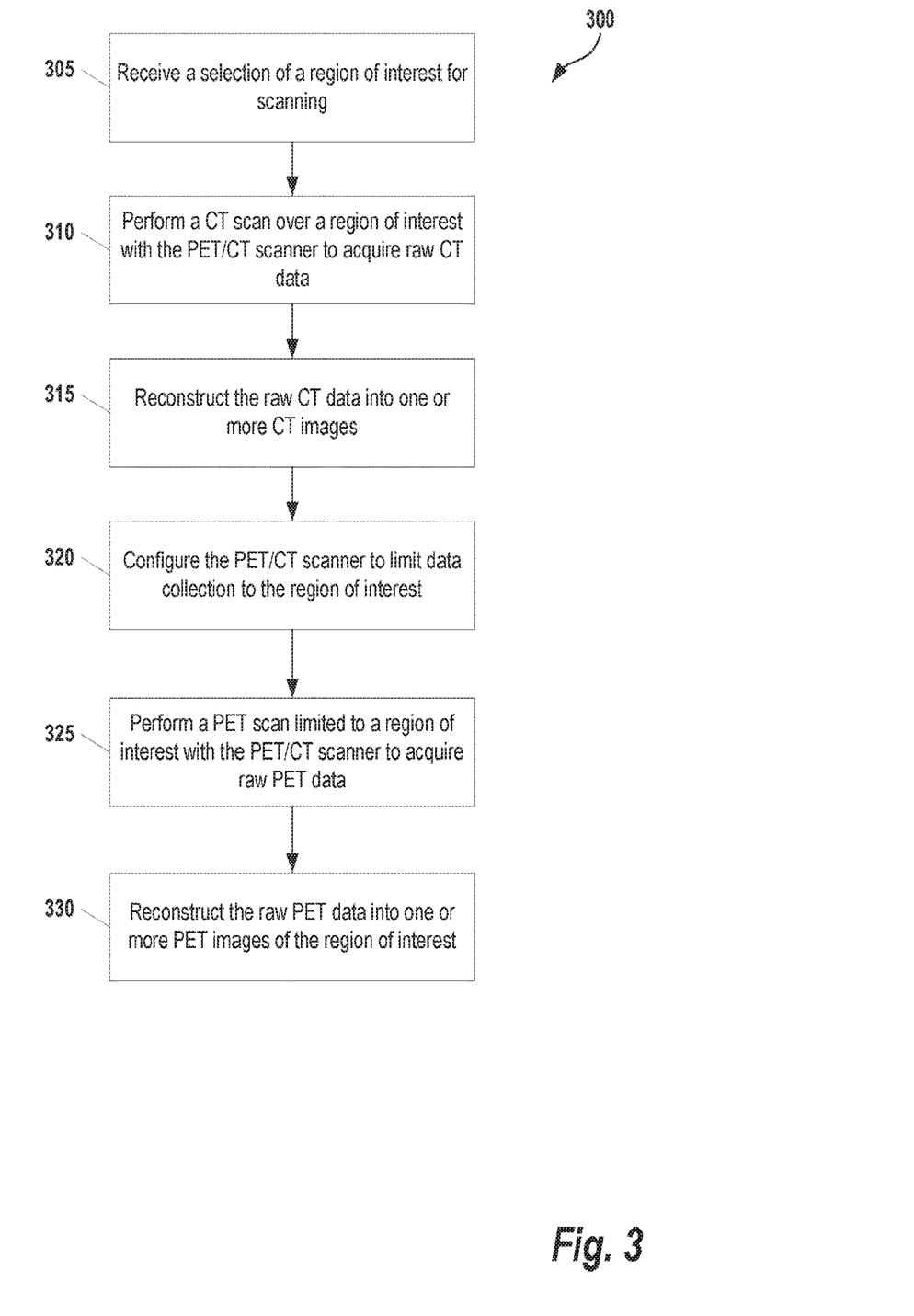
FIG. 3 shows an example method for performing a partial scan of a patient using a PET/CT system, according to some embodiments.

FIG. 3 show an example method 300 for performing a partial scan of a patient using a PET/CT system, according to some embodiments. This method 300 may be performed, for example, by the combined PET and X-Ray CT tomograph shown in FIGS. 1, 2A, and 2B. Briefly, the PET detectors are disabled axially or at the pair production stage, to create a sub-scanner within the PET/CT system. Aside from reducing the overall file size associated with the reconstructed images, the method 300 described in FIG. 3 also provides more efficient data throughput in general and creates smaller listmode and sinogram files during the data collection stage.

Starting at step 305 of FIG. 3, the system receives a selection of a region of interest for scanning. Various techniques may be used to interact with the user and collect this selection. For example in some embodiments, a topogram of a patient's body is acquired using the combined PET/CT system. This topogram is presented on the operator console to a user, and the user selection of the region of interest for scanning is received via the operator console. In one of these embodiments, a series of blocks are presented on the operator interface extending axially along at least one side of the topogram. Each block in the series corresponds to a portion of the topogram. An example of this interface is presented in FIG. 6. The user selection of the region of interest then comprises a selection of one or more of the blocks (e.g., via clicking on the block(s) of interest). In another embodiment, the user selection of the region of interest comprises one or more shapes drawn by a user on one or more portions of the topogram. As an another alternative, in some embodiments, the selection of the region of interest is performed automatically using machine learning. For example, based on the type of study being performed, a machine learning model may analyze an image to locate an organ or tissues of interest and the surrounding area that is needed to perform the desired study.

Continuing with reference to FIG. 3, at step 310, the PET/CT system performs a CT scan over a region of interest to acquire raw CT data and this raw CT data at step 315 into one or more CT images. At step 320, the PET/CT system configured to limit data collection to the region of interest identified in step 305. In some embodiments, a subset of the PET detectors that are outside the region of interest are identified. This identification may be automatically performed by the PET/CT system or an operator may manually identify the detectors. Once these detectors have been identified, the PET/CT system can disable them during collection of the data. Alternatively, in other embodiments, a line-of-response is determined for each coincidence event. The coincidence electronics within the PET/CT system are then configured to only process a subset of the coincidence events having corresponding LORs passing through the region of interest.

Once the PET/CT system has been configured, at step 325 a PET scan limited to a region of interest is performed to acquire raw PET data. In some embodiments, the PET/CT system is configured to satisfy a user-selected ring difference during the scan. As is generally understood in the art, the term "ring difference" refers to the maximal range of axial coincidences in 3D. In other words, the ring difference specifies how many rings away that the rebinning algorithm will accept a coincidence event. Limiting the ring difference reduces randoms and scatters that occur during scanning, thus sharpening the image. However, a small ring difference also decreases the overall number of acquired counts. The ring difference may be specified, for example, as a parameter through the operator console of the combined PET and X-Ray CT tomograph.

Returning to FIG. 3, at step 330, this raw PET data is reconstructed into one or more PET images of the region of interest. The CT and PET images may then be displayed using any technique known in the art. For example in some embodiments, a CT image and a PET image are displayed side-by-side on a graphical user interface (GUI) presented on the operator interface of the PET/CT system. In other embodiments, the aforementioned GUI displays one type of image (i.e., CT or PET) and the GUI includes one or more interface elements (e.g., buttons) that allows the user to selectively alternate between the image types.

Figure 4:
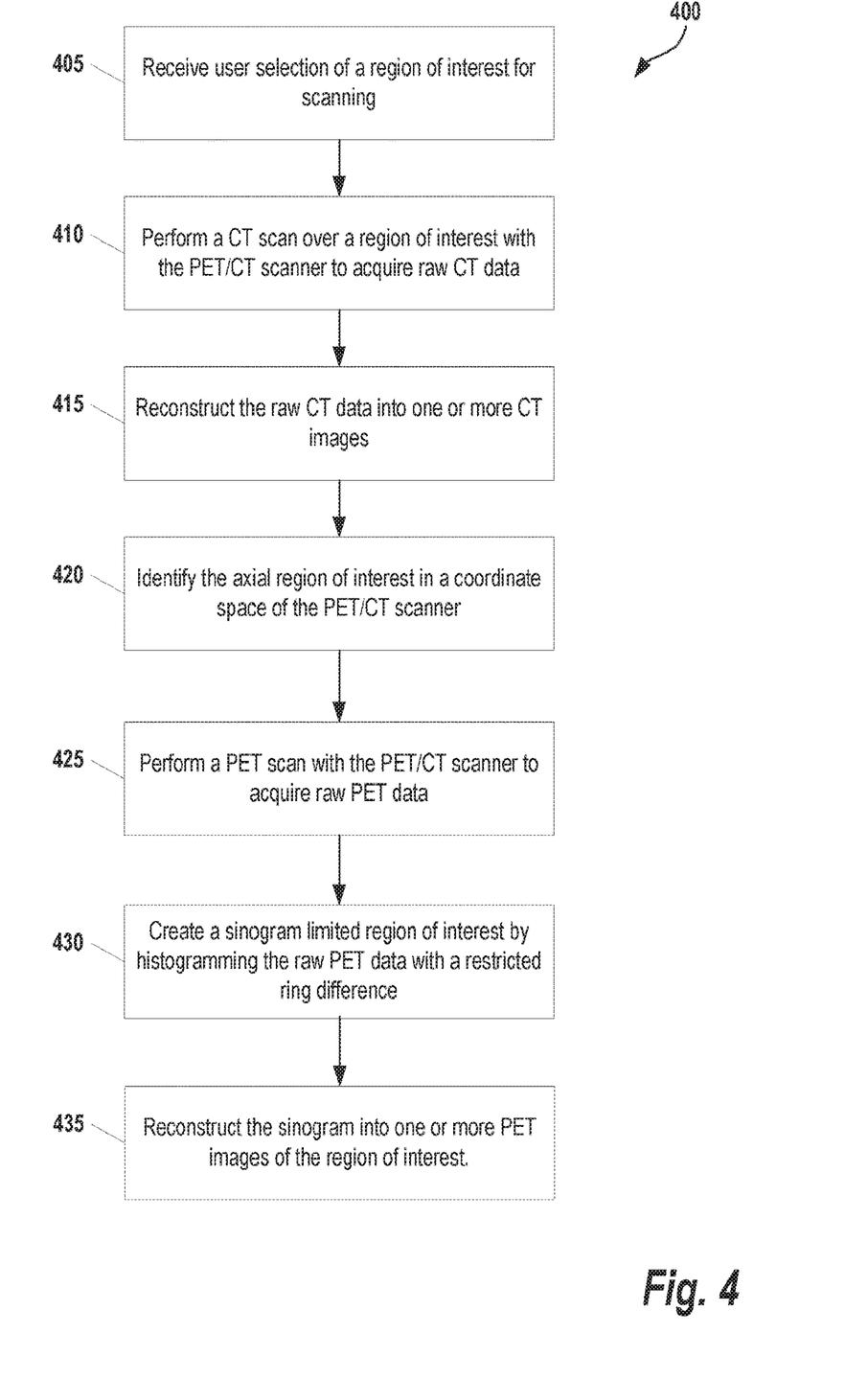
FIG. 4 shows a second method for performing a partial scan of a patient using a PET/CT system, according to some embodiments.

FIG. 4 shows a second method 400 for performing a partial scan of a patient using a PET/CT system, according to some embodiments. This process can be understood as "virtual histogramming." Briefly, the PET/CT system is left in its native state; however histogramming is restricted to create sinograms matching a sub-scanner that only covers the area of interest. As is generally understood in the art, during data collection, a PET scanner bins coincidence events into data arrays according to the event's detected coordinates in space. A sinogram is a matrix into which all found coincidences from a PET scan are histogrammed. Each sinogram comprises 2D, 3D, and event 4D representations of the stream of data collected from the scanner. Each element in the matrix corresponds to the number of valid LORs which have been recorded by a certain pair of opposing detectors. The sinogram is conceptually a line integral of the emission data in which data along a particular radial offset s and angle φ is mapped into a row and column position. With virtual histogramming, the matrix is truncated so that it only includes elements with values of s and φ corresponding to areas of interest. Thus, each area is essentially a "sub-scanner" of the full PET scanner.

Steps 405-415 of the method 400 are performed in a manner similar to steps 305-315 of FIG. 3, discussed above. Briefly, a user selects a region of interest and the PET/CT system acquires and reconstructs CT images of that region. As with the method 300 of FIG. 3, a user may interact with a topogram to identify the region of interest. At step 420, the axial region of interest is identified in a coordinate space of the PET/CT system. This identification comprises radial offset values and a restricted ring difference value (where the restriction is based on LORs which traverse the region to be reconstructed). The PET/CT scanner performs a PET scan at step 425 to acquire the raw PET data.

Next, at step 430, the PET/CT system create a sinogram limited to the region of interest by histogramming the raw PET data with the radial offset values and the restricted ring difference. This may be accomplished in a variety of ways. For example, in some embodiments, a look-up table is used to when creating the sinogram to identify regions for reconstruction. The look-up operation can be restricted based on the radial offset values and the restricted ring difference, and other factors related to the region of interest such as its axial length. Finally, at step 435, the sinogram is reconstructed into one or more PET images of the region of interest.

Figure 5:
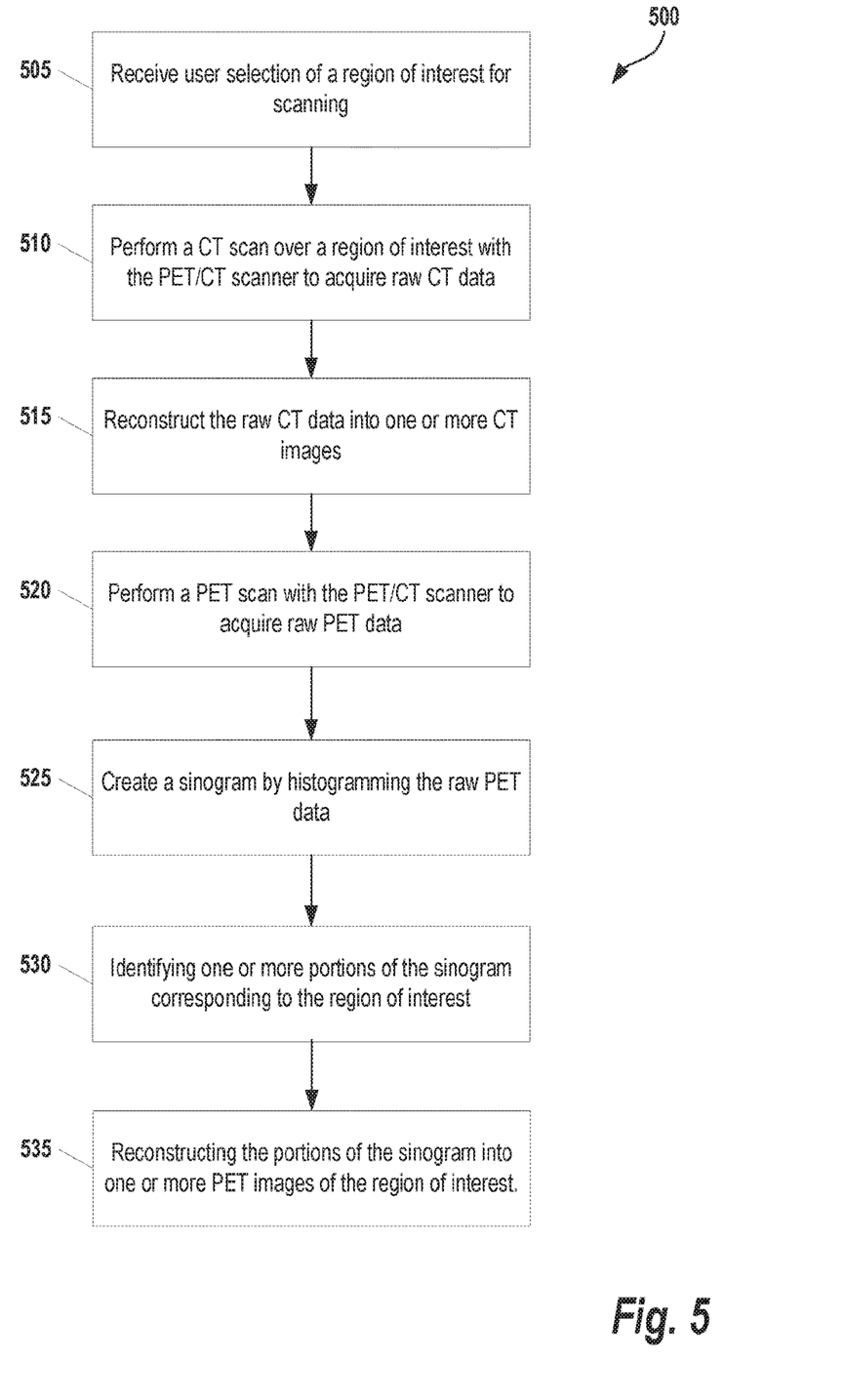
FIG. 5 shows a third method for performing a partial scan of a patient using a PET/CT system.

FIG. 5 shows a third method 500 for performing a partial scan of a patient using a PET/CT system. Briefly, the PET/CT system is left in its native state; however the reconstructed volume is restricted. Reconstruction is performed after acquisition of the PET data in sonograms to estimate a distribution of the in vivo tracer in the patient's anatomy. Steps 505-515 are performed in a manner similar to steps 305-315 and steps 405-415 in FIGS. 3 and 4, respectively. At step 520, the PET/CT system performs a PET scan with the PET/CT system to acquire raw PET data. The PET/CT system creates a sinogram at step 525 by histogramming the raw PET data. Next, at step 525, the PET/CT system identifies one or more portions of the sinogram corresponding to the region of interest. Then, at step 530, the portions of the sinogram are reconstructed into one or more PET images of the region of interest.

In some embodiments, as an alternative to using a sinogram to perform the reconstruction, reconstruction is performed directly on the stream of data collected from the PET/CT scanner. This is referred to as "listmode reconstruction." Because the crystal pairs for the volume of interest are known, the approaches discussed above for restricting the data acquired or processed may be similarly applied to listmode reconstruction.

Figure 6:
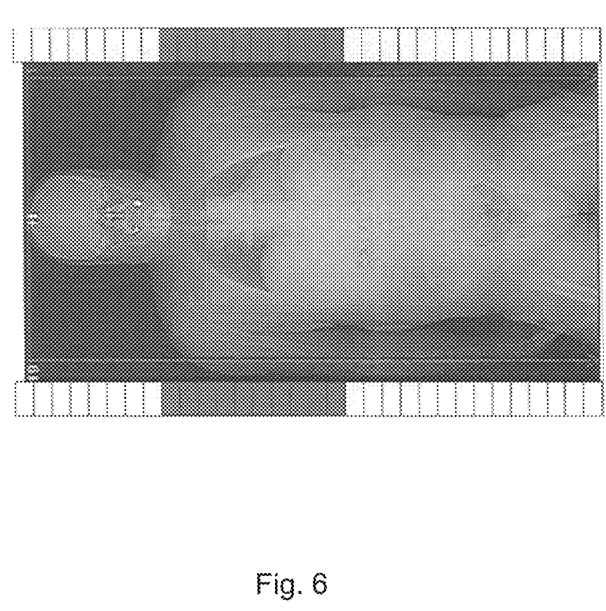
FIG. 6 shows an example topogram interface utilized in some embodiments for selecting a region of interest.
Figure 7A:
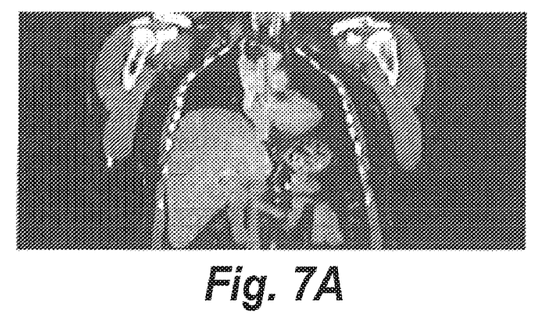
FIG. 7A shows a CT image for an example region of interest.
Figure 7B:
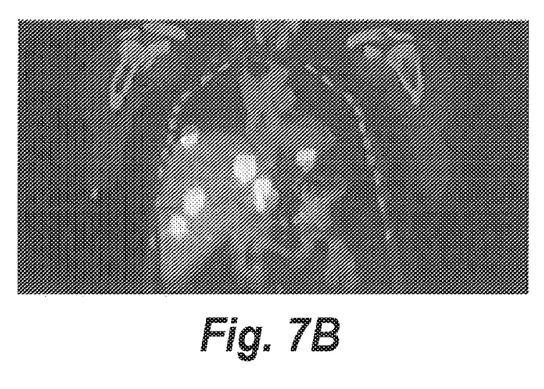
FIG. 7B shows a PET image for the example region of interest.

FIG. 6 shows an example topogram interface utilized in some embodiments for selecting a region of interest. Boxes extend along the side of the topogram. As shown in FIG. 6, as certain boxes are selected they change color to indicate that the corresponding anatomical region should be designated as a region of interest. In this example, the middle region of the patient is selected. FIGS. 7A and 7B show the CT image and PET image, for this region.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing systems, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity. Also, while some method steps are described as separate steps for ease of understanding, any such steps should not be construed as necessarily distinct nor order dependent in their performance.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f) unless the element is expressly recited using the phrase "means for."

We claim:

1. A method for performing a partial scan of a patient using a PET/CT system, the method comprising:
receiving a selection of a region of interest for scanning;
performing a CT scan over a region of interest with the PET/CT system to acquire raw CT data;
reconstructing the raw CT data into one or more CT images;
performing a PET scan with the PET/CT system to acquire raw PET data comprising a plurality of coincidence events;
for each coincidence event, determining a corresponding line-of-response (LOR) for the coincidence event, the determined LORs including LORS passing through the region of interest and LORs not passing through the region of interest; and
reconstructing the raw PET data into one or more PET images of the region of interest using only the coincidence events having corresponding LORs passing through the region of interest.

2. The method of claim 1, further comprising:
acquiring a topogram of a patient's body using the combined PET/CT system; and
presenting the topogram on the operator console to a user, wherein the selection of the region of interest for scanning is received via the operator console.

3. The method of claim 2, further comprising:
presenting, on the operator console, a series of blocks extending axially along at least one side of the topogram,
wherein each block in the series corresponds to a portion of the topogram; and
wherein the selection of the region of interest comprises a selection of one or more of the blocks.

4. The method of claim 2, wherein the selection of the region of interest comprises one or more shapes drawn by a user on one or more portions of the topogram.

5. The method of claim 1, further comprising:
identifying a subset of the PET detectors that are outside the region of interest; and
configuring the PET/CT system such that the subset of PET detectors are disabled during acquisition of the raw PET data.

6. The method of claim 1, further comprising:
receive a selection of a ring difference associated with the PET/CT system; and
configuring the PET/CT system to satisfy the ring difference during the PET scan.

7. A method for performing a partial scan of a patient using a PET/CT system, the method comprising:
  receiving a selection of a region of interest for scanning;
  performing a CT scan over the region of interest with the PET/CT system to acquire raw CT data;
  reconstructing the raw CT data into one or more CT images;
  identifying, based on the one or more CT images, one or more radial offset values and a restricted ring difference describing the region of interest in a coordinate space of the PET/CT system;
  performing a PET scan with the PET/CT system to acquire raw PET data; and
  reconstructing one or more PET images from the raw PET data limited to the region of interest to yield.

8. The method of claim 7, further comprising:
  acquiring a topogram of a patient's body using the combined PET/CT system; and
  presenting the topogram on the operator console to a user, wherein the selection of the region of interest for scanning is received via the operator console.

9. The method of claim 8, further comprising:
  presenting, on the operator console, a series of blocks extending axially along at least one side of the topogram,
  wherein each block in the series corresponds to a portion of the topogram; and
  wherein the selection of the region of interest comprises a selection of one or more of the blocks.

10. The method of claim 7 wherein reconstructing the one or more PET images comprises applying a listmode reconstruction directly to the raw PET data.

11. The method of claim 7, wherein reconstructing the one or more PET images comprises:
  creating a sinogram limited to the region of interest by histogramming the raw PET data using the radial offset values and the restricted ring difference; and
  reconstructing the sinogram into the PET images.

12. A method for performing a partial scan of a patient using a PET/CT system, the method comprising:
  receiving a selection of a region of interest for scanning;
  performing a CT scan over the region of interest with the PET/CT system to acquire raw CT data;
  reconstructing the raw CT data into one or more CT images;
  performing a PET scan with the PET/CT system to acquire raw PET data comprising a plurality of coincidence events;
  for each coincidence event, determining a corresponding line-of-response (LOR) for the coincidence event, the determined LORs including LORs which pass through the region of interest and LORs which do not pass through the region of interest, and
  performing a reconstruction of the raw PET data using only the coincidence events having corresponding LORS which pass through the region of interest to yield one or more PET images.

13. The method of claim 12, further comprising:
  acquiring a topogram of a patient's body using the combined PET/CT system; and
  presenting the topogram on the operator console to a user, wherein the selection of the region of interest for scanning is received via the operator console.

14. The method of claim 13, further comprising:
  presenting, on the operator console, a series of blocks extending axially along at least one side of the topogram,
  wherein each block in the series corresponds to a portion of the topogram; and
  wherein the selection of the region of interest comprises a selection of one or more of the blocks.

15. The method of claim 12 wherein the reconstruction is a listmode reconstruction directly applied to the raw PET data.

16. The method of claim 12, wherein the reconstruction is performed by:
  creating a sinogram limited to the region of interest by histogramming the raw PET data using the radial offset values and the restricted ring difference; and
  reconstructing the sinogram into the PET images.

17. A system for performing a partial scan of a patient, the system comprising:
  one or more operator consoles configured to receive a selection of a region of interest for scanning;
  a computed tomography (CT) subsystem configured to:
    perform a CT scan over & the region of interest to acquire raw CT data, and
    reconstruct the raw CT data into one or more CT images; and
  a Positron-Emission Tomography (PET) subsystem comprising PET detectors and configured to:
    identify a subset of the PET detector that are outside the region of interest,
    disable the identified PET detectors,
    while the identified PET detectors are disabled, perform a PET scan limited to the region of interest to acquire raw PET data, and
    reconstruct the raw PET data into one or more PET images of the region of interest.

18. The system of claim 17, wherein the hardware elements comprise one or more processors and the PET subsystem is configured to:
  for each coincidence event of the raw PET data, determine a corresponding line-of-response (LORs);
  configure the one or more processors to process only the coincidence events having corresponding LORs passing through the region of interest.

* * * * *